(12) United States Patent
Xu et al.

(10) Patent No.: US 11,098,281 B2
(45) Date of Patent: Aug. 24, 2021

(54) METHOD OF DIFFERENTIATING PLURIPOTENT STEM CELLS INTO MESENCHYMAL STEM CELLS UNDER 3D SPHEROIDAL CULTURE CONDITIONS

(71) Applicant: University of Macau, Macau (CN)

(72) Inventors: Ren-He Xu, Macau (CN); Bin Jiang, Macau (CN); Li Yan, Macau (CN)

(73) Assignee: UNIVERSITY OF MACAU, Macau (CN)

( * ) Notice: Subject to any disclaimer, the term of this patent is extended or adjusted under 35 U.S.C. 154(b) by 304 days.

(21) Appl. No.: 16/041,518

(22) Filed: Jul. 20, 2018

(65) Prior Publication Data
US 2019/0112573 A1    Apr. 18, 2019

(30) Foreign Application Priority Data

Oct. 17, 2017  (CN) .......................... 201710965622.1

(51) Int. Cl.
*C12N 5/00* (2006.01)
*C12N 5/0775* (2010.01)
*A61K 9/00* (2006.01)
*A61K 35/28* (2015.01)

(52) U.S. Cl.
CPC .......... *C12N 5/0062* (2013.01); *A61K 9/0019* (2013.01); *A61K 35/28* (2013.01); *C12N 5/0662* (2013.01); *C12N 5/0668* (2013.01); *C12N 2500/32* (2013.01); *C12N 2501/15* (2013.01); *C12N 2501/155* (2013.01); *C12N 2501/999* (2013.01); *C12N 2506/02* (2013.01); *C12N 2506/025* (2013.01); *C12N 2509/00* (2013.01); *C12N 2513/00* (2013.01)

(58) Field of Classification Search
CPC .................................................. C12N 5/0062
See application file for complete search history.

(56) References Cited

U.S. PATENT DOCUMENTS 8,445,273 B2 * 5/2013 Green .................. C12N 5/0606
                                                                435/363

FOREIGN PATENT DOCUMENTS

WO    WO-2013077423 A1 *  5/2013 ........... C12N 5/0606

OTHER PUBLICATIONS

Wang et al. (ePub Nov. 2, 2015, Stem Cell, vol. 34, pp. 380-391) (Year: 2015).*
English Translation of WO 2013/077423 A1 (Year: 2013).*
Wang, et al., "Immune Modulatory Mesencmal Stem Cells Derived from Human Embryonic Stem Cells Through a Trophoblast-Like Stage", Stem Cells, Nov. 2, 2015, pp. 380-391.

* cited by examiner

*Primary Examiner* — Thaian N. Ton
*Assistant Examiner* — David A Montanari
(74) *Attorney, Agent, or Firm* — Snell & Wilmer L.L.P.

(57) ABSTRACT

A method of differentiating pluripotent stem cells into mesenchymal stem cells, a culture medium used in the method of differentiating pluripotent stem cells into mesenchymal stem cells and a method of performing tissue and organ regeneration by using the mesenchymal stem cells obtained by differentiation using the method of differentiating pluripotent stem cells into mesenchymal stem cells are provided. The method of differentiating pluripotent stem cells into mesenchymal stem cells comprises differentiating, completely under 3D suspension conditions, pluripotent stem cells into trophoblast-like cells using BMP4 and A8301, and then differentiating the trophoblast-like cells into mesenchymal stem cells. Neither of two differentiation processes needs passaging or replacement of a culture container.

9 Claims, 2 Drawing Sheets

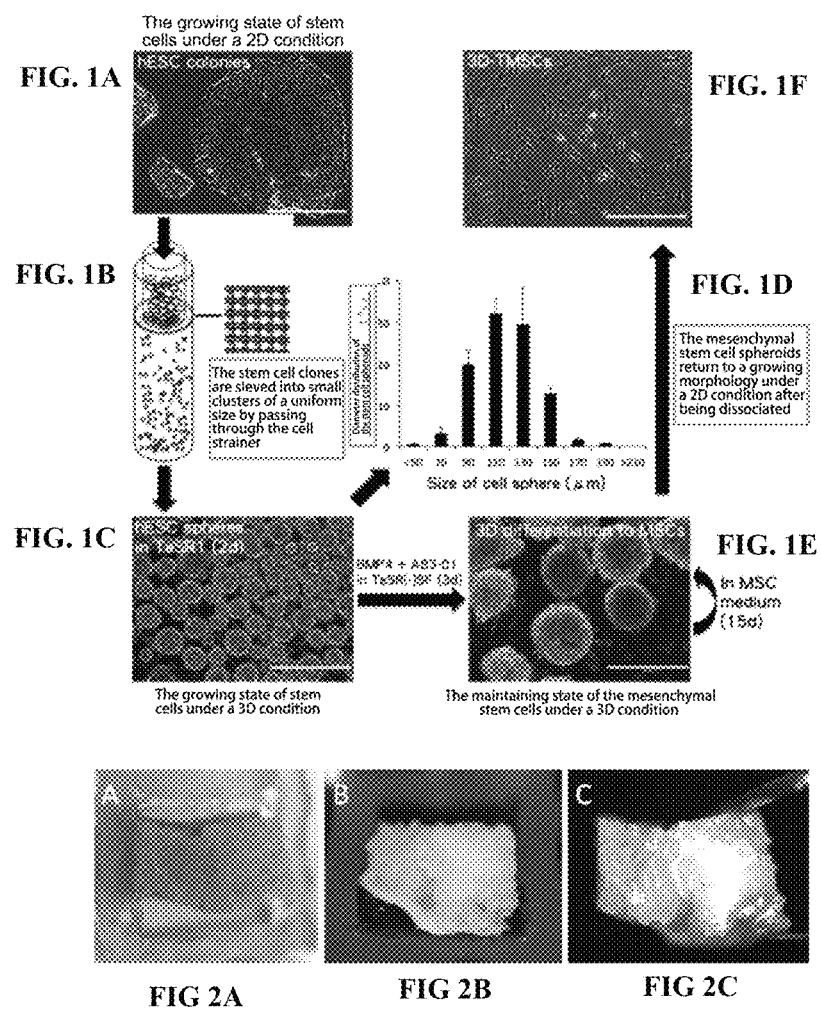

METHOD OF DIFFERENTIATING PLURIPOTENT STEM CELLS INTO MESENCHYMAL STEM CELLS UNDER 3D SPHEROIDAL CULTURE CONDITIONS

CROSS-REFERENCE TO RELATED APPLICATIONS

This application claims priority to Chinese Patent Application No. 201710965622.1, filed on Oct. 17, 2017 with the Chinese Patent Office and entitled "Method of Differentiating Pluripotent Stem Cells into Mesenchymal Stem Cells and Culture Medium and Use thereof", the contents of which are herein incorporated by reference in their entirety.

TECHNICAL FIELD

The present disclosure relates to the field of cell biology, and particularly to a method of differentiating pluripotent stem cells into mesenchymal stem cells and culture medium and use thereof.

BACKGROUND ART

Mesenchymal stem cells are cells having a potential of multi-directional differentiation, and exist in umbilical cord blood, placenta, fat, bone marrow blood and connective tissues. Mesenchymal stem cells are usually in a resting state, and when the human body requires repairing for trauma, they will be activated by the immune system, and migrate to an injured site to proliferate and differentiate into corresponding cells, so as to inhibit inflammatory response, promote vascular regeneration and directly participate in the repair process. The mesenchymal stem cells are important components for tissue and organ regeneration of human bodies after birth. The mesenchymal stem cells can be isolated from adult tissues, and studies have confirmed that they can be differentiated into fat, bones and chondrocytes and even neural precursor cells under a specific environment in vitro, moreover, they also have a wide range of immune-regulation functions, can activate the proliferation of Treg cells, and inhibit activities of T and B lymphocytes. The mesenchymal stem cells not only promote tissue regeneration, but also can be applied to autoimmune diseases as well as graft-versus-host-disease and immunological rejection after organ transplantation, and have achieved remarkable therapeutic effects.

Although mesenchymal stem cells isolated from adult tissues have good effects, they still have some disadvantages that are difficult to be overcome. Firstly, they rely on volunteer donors, and the collection of tissues is not an enjoyable experience for the donors. Moreover, the isolation process of the mesenchymal stem cells is accompanied with unfavorable factors such as small amount, long time, high costs, and difficulty for quality control, which are difficult to overcome. Isolated mesenchymal stem cells can hardly be amplified in large amount in vitro, and the process requires high costs, the cells would easily senesce and would degenerate very fast, which cannot meet clinical requirements sufficiently, and thereby limits their applicable range and effect.

Pluripotent stem cells, such as embryonic stem cells, are cells that can always be self-renewed while keeping a potential of differentiation into various somatic cells. The pluripotent stem cells have a stronger proliferative ability and a broader differentiation potential than the mesenchymal stem cells, and can also be directionally differentiated into the mesenchymal stem cells under specific conditions. The embryonic stem cells have a stronger differentiation ability, longer telomeres and more active telomere transferases than the mesenchymal stem cells, and thus can be proliferated and amplified in vitro more easily, and constantly produce the mesenchymal stem cells, which satisfies requirements of tissue regeneration and immunomodulation. Moreover, compared with adult tissue-derived mesenchymal stem cells, embryonic stem cell-derived mesenchymal stem cells (EMSCs) have lower expression of IL-6, higher expression of IL-8 and lower expression of HLA, thus have lower immunogenicity, and are more advantageous for allogeneic treatment.

At present, the in vitro differentiation of the pluripotent stem cells into the mesenchymal stem cells is carried out by adherent culturing in a 2D state, which has a relatively low efficiency, and requires 3-5 procedures and multiple times of passaging, wherein flask change is necessary for the culture, which has relatively high costs.

DISCLOSURE OF THE INVENTION

A first object of the present disclosure is to provide a method of differentiating pluripotent stem cells into mesenchymal stem cells completely under a 3D suspension condition, such that, compared with adherent culturing, this method is less time-consuming and highly efficient, and the mesenchymal stem cells produced by differentiation have more excellent proliferation in vitro ability, are not prone to senescence, and have stronger anti-apoptotic ability.

A second object of the present disclosure is to provide a culture medium, so as to realize culturing of differentiation of pluripotent stem cells into mesenchymal stem cells, which process is less time-consuming and highly efficient, and the mesenchymal stem cells produced by differentiation have more excellent proliferation in vitro ability, are not prone to senescence, and have stronger anti-apoptotic ability.

A third object of the present disclosure is to provide use of mesenchymal stem cells obtained by differentiation of the above method of differentiating pluripotent stem cells into mesenchymal stem cells in tissue and organ regeneration, such that the mesenchymal stem cells can quickly promote tissue and organ regeneration.

The following technical solutions are used in the present disclosure for solving the technical problems thereof.

A method of differentiating pluripotent stem cells into mesenchymal stem cells provided in the present disclosure includes: abundantly amplifying pluripotent stem cells using a 3D suspension culturing system, then differentiating the pluripotent stem cells into trophoblast-like cells using BMP4 and A8301, then differentiating the trophoblast-like cells into mesenchymal stem cells, wherein two differentiation processes are both suspension culturing carried out in a form of cell spheroids, and no passaging or replacement of a culture container is needed in the whole processes.

The present disclosure further relates to a culture medium used in the above method of differentiating pluripotent stem cells into mesenchymal stem cells, which culture medium includes a first cell differentiation culture medium and a second cell differentiation culture medium, wherein the first cell differentiation culture medium includes BMP4, A8301 and a basal culture medium, and the basal culture medium includes, in parts by weight, 72-76 parts of a Dulbecco's modified eagle medium (DMEM) low-sugar culture medium, 18-22 parts of serum substitute, 0.5-1.5 parts of non-essential amino acid and 3-7 parts of L-Glutamine; and the second cell differentiation culture medium is the basal culture medium.

The present disclosure further relates to use of mesenchymal stem cells obtained by differentiation with the above method of differentiating pluripotent stem cells into mesenchymal stem cells for tissue and organ regeneration.

Compared with the method of obtaining the mesenchymal stem cells in a 2D differentiation manner, the method of differentiating pluripotent stem cells into mesenchymal stem cells in the present disclosure is less time-consuming and highly efficient, has high differentiation purity, and the obtained mesenchymal stem cells have more excellent proliferation in vitro ability, are not prone to senescence, and have stronger anti-apoptotic ability. Moreover, with the spheroidal property of the mesenchymal stem cells, it can be assured that the mesenchymal stem cells can survive for one week at a room temperature, while the biological activity thereof will not be affected. The survival rate at a room temperature after 7-10 days is up to 90%, and after restoration to conventional culture conditions, they still have a growth rate similar to that of normal control cells, a lower senescence degree and similar biological functions including the ability of directional differentiation into various tissues such as bone, cartilage and fat and immunomodulation functions.

BRIEF DESCRIPTION OF DRAWINGS

In order to more clearly illustrate technical solutions of embodiments of the present disclosure, figures which are needed for description of the embodiments will be introduced briefly below. It should be understood that the figures below merely show some examples of the present disclosure, and therefore should not be considered as limiting the scope. A person ordinarily skilled in the art still can obtain other relevant figures according to these figures, without paying inventive efforts.

FIG. 1 is a schematic diagram of differentiating a pluripotent stem cell line Envy into mesenchymal stem cells under 3D spheroidal suspension conditions in Example 1.

FIG. 1A shows monolayer-cultured human pluripotent stem cells;

FIGS. 1B, C, D, E, F, in turn, show a schematic diagram of preparing stem cell spheroids through a slicing method by means of a cell strainer, a diagram of a growing state of stem cells under 3D conditions under a microscope, a graph of diameter distribution of the cell spheroids, a maintaining state of the mesenchymal stem cells under 3D conditions and the morphology of the mesenchymal stem cell spheroids returning to a growing state under 2D conditions after being dissociated;

FIG. 2 is a process diagram of perfusion of the mesenchymal stem cell spheroids into a bone fibrous scaffold for carrying out bone regeneration experiments;

FIG. 2A shows two human bone fibrous scaffolds;

FIG. 2B shows the mesenchymal stem cells sufficiently infiltrating into the internal and connection of the two fibrous scaffolds in FIG. 2A;

FIG. 2C shows the mesenchymal stem cells sufficiently fusing the two fibrous scaffolds in FIG. 2A after osteogenic differentiation for 20 days;

DETAILED DESCRIPTION OF EMBODIMENTS

Figure 3:
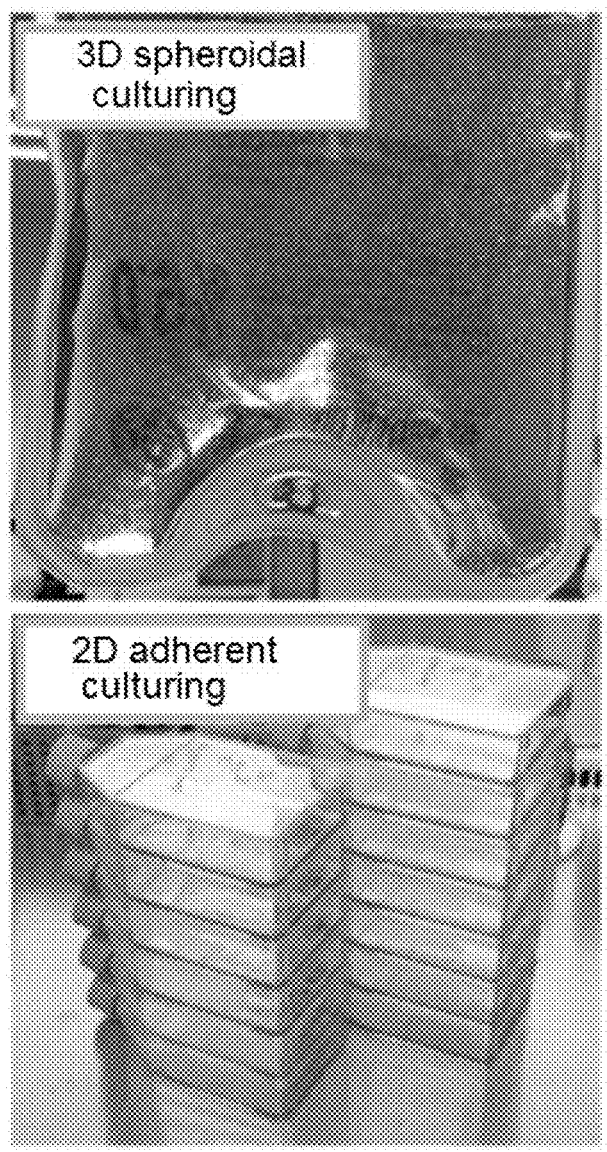
FIG. 3 is a comparison diagram of 3D suspension culturing and 2D adherent culturing.

In order to make the objects, technical solutions and advantages of the embodiments of the present disclosure clearer, below the technical solutions in the embodiments of the present disclosure will be described clearly and completely. If no specific conditions are specified in the embodiments or the examples, they are carried out under normal conditions or conditions recommended by the manufacturer. If manufacturers of reagents or apparatus used are not specified, they are conventional products commercially available.

Below a method of differentiating pluripotent stem cells into mesenchymal stem cells and culture medium and use thereof in the embodiments of the present disclosure are described specifically.

Some embodiments of the present disclosure provide a method of differentiating pluripotent stem cells into mesenchymal stem cells, which includes: differentiating pluripotent stem cells into trophoblast-like cells using BMP4 and A8301, then differentiating the trophoblast-like cells into mesenchymal stem cells, wherein two differentiation processes are both suspension culturing carried out in a form of cell spheroids.

In the above, bone morphogenetic protein-4 (BMP4) is also named BMP-2b, belonging to TGF-β superfamily. BMP4 is homologic with BMP-2, and has structural and functional similarities. BMP4 is not only an osteoinduction active factor with superpowers, but also an important regulatory factor for embryonic development of nervous systems, growth and differentiation, and development of lungs. A8301 is a signal pathway inhibitor, and it can remarkably promote an MET process in an early stage of reprogramming, and further promote reprogramming efficiency of somatic cells.

Some embodiments of the present disclosure provide a method of differentiating pluripotent stem cells into mesenchymal stem cells, which includes: placing pluripotent stem cells in a first cell differentiation culture medium containing BMP4 and A8301 to carry out first differentiation culturing, then carrying out second differentiation culturing in a second cell differentiation culture medium for the trophoblast-like cells obtained in the first differentiation culturing, to obtain mesenchymal stem cells.

According to some embodiments, the first differentiation culturing lasts for 2-5 days, during which period the pluripotent stem cells can be well differentiated into the trophoblast-like cells, and the second differentiation culturing lasts for 18-22 days.

According to some embodiments, culture conditions of the two times of differentiation are 36-39° C., 4-7% carbon dioxide and 85-92% humidity.

BMP4 and A8301 are key components for stable differentiation of pluripotent stem cells, therefore, their concentrations also have relatively great influences on differentiation effects of the pluripotent stem cells, and according to some embodiments, the concentration of BMP4 in the first cell differentiation culture medium is 5-15 ng/mL, preferably 6-13 ng/mL, and more preferably 8-12 ng/mL, and the concentration of A8301 in the first cell differentiation culture medium is 0.5-1.5 μM, preferably 0.6-1.3 μM, and more preferably 0.8-1.2 μM.

According to some embodiments, the first cell differentiation culture medium includes BMP4, A8301 and a basal culture medium, and the basal culture medium includes, in parts by weight, 72-76 parts of a DMEM low-sugar culture medium, 18-22 parts of serum substitute, 0.5-1.5 parts of non-essential amino acid and 3-7 parts of L-Glutamine; the second cell differentiation culture medium is the basal culture medium. The serum substitute is a conventional serum substitute in the market, for example, KSR serum substitute. The non-essential amino acid includes glutamic acid, alanine, glycine, asparaginic acid, cystine, proline, serine, tyrosine and so on.

According to some embodiments, the pluripotent stem cells are obtained through amplification culturing of initial pluripotent stem cells, and the amplification culturing of the initial pluripotent stem cells comprises cutting cell colonies of the initial pluripotent stem cells with a cell strainer into cell clusters, and then performing suspension culturing on the cell clusters in an amplification culture medium. The pluripotent stem cells are abundantly amplified to a desired amount, e.g. no less $10^9$, in a non-adherent type culture container by utilizing the property of the pluripotent stem cells that they are spheroidized and proliferated in large amount under 3D suspension culture conditions, and then they are directionally differentiated into mesenchymal stem cells. It should be indicated that in other embodiments, the pluripotent stem cells also can be directly acquired. The initial pluripotent stem cells refer to pluripotent stem cells that are not subjected to amplification culturing in a manner of suspension culturing.

Effects of the amplification culturing can be better by carrying out the amplification culturing for a plurality of cell clusters of similar shapes and sizes, and cells obtained after the amplification have better biological properties. Furthermore, a process of the amplification culturing is present in a spheroidal morphology, and since it is a suspension culturing process, there is no need to change a culture container, which facilitates process control and standardized production, and also can have a reduced period of culturing.

According to some embodiments, in the process of suspension culturing of the cell clusters, a tackifier, a matrigel, a hydrogel or a thickening agent is added, and by adding the tackifier, the matrigel, the hydrogel or the thickening agent, it can be ensured that in the culturing process, the stem cell spheroids do not fuse therebetween, thereby preventing formation of irregular shapes and occurrence of quality degradation due to spontaneous differentiation.

In some embodiments, the tackifier is a food-grade additive, and the food-grade tackifier will not result in a production of biotoxicity, is able to be metabolized, leaves no residue behind, has a high level of safety, and is convenient to use. Preferably, the tackifier is methylcellulose, having another name of methyl cellulose, and it is white or off-white fibrous or granular powder, without odor or taste. The methylcellulose swells in water into a clear or slightly muddy colloidal solution. Preferably, a concentration of the added methylcellulose is 0.2%-0.5% of a mass of the amplification culture medium. Within this concentration range, not only the cell spheroids will not fuse therebetween, but also no unfavorable influences will be generated to the amplification culturing of the cells due to a too high concentration.

According to some embodiments, the amplification culture medium is an mTeSR1 cell culture medium, and the mTeSR1 cell culture medium is added with Y27632, wherein Y27632 is a widely used small-molecule specific inhibitor of a serine-threonine protein kinase (ROCK) family formed by efficient Rho-related frizzled proteins.

According to some embodiments, a concentration of Y27632 in the mTeSR1 cell culture medium is 8-12 µM.

According to some embodiments, the cell strainer has a pore size (mesh size) of 50 microns, and the cell clusters formed through sieving with the cell strainer with this pore size can be subjected to better amplification culturing, facilitating the conduction of the whole suspension culturing.

According to some embodiments, the cell colonies of the initial pluripotent stem cells are collected after the initial pluripotent stem cells are adherently cultured to a degree of fusion of 78-82% and then washed with 1× PBS. The initial pluripotent stem cells refer to pluripotent stem cells originally obtained from the human body or originally obtained. PBS is a phosphate buffer saline, generally used as a solvent, and serves a function of dissolving protective agents. A 1× PBS buffer solution is just configured with PBS of 0.1M. The cell colonies obtained after being washed with 1× PBS can maintain their integrated biological activity.

Some embodiments of the present disclosure further provide a method of differentiating pluripotent stem cells into mesenchymal stem cells, which specifically includes:

S1. Amplification Culturing of Pluripotent Stem Cells

The pluripotent stem cells are amplified in a 3D spheroidal suspension culture system, and the pluripotent stem cells naturally form spheroids under non-adherent conditions. Specifically, cell colonies that are detached after 2D adherent culturing are sieved with a cell strainer to form cell clusters of similar sizes. Then the cell clusters gradually form cell spheroids through suspension culturing.

S2. Differentiation Culturing

Two times of differentiation culturing are carried out for the pluripotent stem cells obtained after the amplification, wherein for a first time of differentiation culturing: the pluripotent stem cells are differentiated for 2-5 days using BMP4 and A8301 to obtain trophoblast-like cells, and for a second time of differentiation culturing: the trophoblast-like cells are differentiated for 18-22 days into the mesenchymal stem cells, wherein processes of the two times of differentiation culturing are both suspension culturing carried out in a form of cell spheroids.

S3. Packaging for Use

The differentiated mesenchymal stem cell spheroids are packaged in a cell container such as a centrifuge tube, with up to 90% of a space within the container being filled with a stem cell culture medium, and stored and transported at a room temperature.

Some embodiments of the present disclosure further relate to a culture medium used in the above method of differentiating pluripotent stem cells into mesenchymal stem cells, which includes a first cell differentiation culture medium and a second cell differentiation culture medium, wherein the first cell differentiation culture medium includes BMP4, A8301 and a basal culture medium, and the basal culture medium includes, in parts by weight, 72-76 parts of a DMEM low-sugar culture medium, 18-22 parts of serum substitute, 0.5-1.5 parts of non-essential amino acid and 3-7 parts of L-Glutamine; the second cell differentiation culture medium is the basal culture medium. The serum substitute is a conventional serum substitute in the market, for example, KSR serum substitute. The non-essential amino acid includes glutamic acid, alanine, glycine, asparaginic acid, cystine, proline, serine, tyrosine and so on.

According to some embodiments, a concentration of BMP4 in the first cell differentiation culture medium is 5-15 ng/mL, preferably 6-13 ng/mL, and more preferably 8-12 ng/mL, and a concentration of A8301 in the first cell differentiation culture medium is 0.5-1.5 µM, preferably 0.6-1.3 µM, and more preferably 0.8-1.2 µM.

Some embodiments of the present disclosure further relate to use of mesenchymal stem cells obtained by differentiation with the above method of differentiating pluripotent stem cells into mesenchymal stem cells for tissue and organ regeneration.

According to some embodiments, the mesenchymal stem cells obtained from the differentiation are packaged in a cell container, up to 89-91% of an internal space of the cell container is filled with a stem cell culture medium, and preferably, a material of the cell container is glass or plastic. The cell container can be a culture bag, and also can be a culture flask. When the stem cell spheroids are produced by utilizing a culture flask, the culture flask can be placed vertically for the culturing, and after the culturing is completed, stem cell spheroids are washed by adding 1× PBS from a mouth of the flask, and then can be used after being collected.

It should be indicated that during the packaging of the mesenchymal stem cell spheroids, the production of air bubbles due to mixing of gas should be avoided. During transportation, what is required is just to place the cell container under a room temperature, with a temperature ranging from 10° C. to 35° C., and intense light exposure, high temperature (higher than 42° C.) and low temperature (lower than 0° C.) should be avoided.

According to some embodiments, the differentiated mesenchymal stem cell spheroids are packaged in a cell container such as a centrifuge tube, and storage and transportation can be realized at a room temperature as long as up to 90% of the space within the container is filled with the stem cell culture medium. If a culture flask is used, a flask cap can be directly tightened. The mesenchymal stem cell spheroids can maintain a motility rate of no less than 90% within 10 days and assure an excellent biological function, and after reaching a use site, the mesenchymal stem cells can be directly used in a form of spheroidal shape for tissue and organ regeneration and the like.

According to some embodiments, when the mesenchymal stem cells are intravascularly injected, the mesenchymal stem cells are digested and dissociated into single cells for injection.

According to some embodiments, the digesting and dissociating the mesenchymal stem cells into single cells includes mixing the mesenchymal stem cells with trypsin for digestion, and preferably, a percentage by volume of the trypsin is 0.05-0.25% of the mesenchymal stem cells, and the digestion lasts at least 10 minutes, such that the mesenchymal stem cells can be digested and dissociated into single cells, further, when the mesenchymal stem cells are injected into vessels, they can play a better role.

According to some embodiments, after the mesenchymal stem cells are digested with trypsin, and then subjected to trypsin neutralization and stem cell centrifugation in sequence, and according to some embodiments, a solution for carrying out the trypsin neutralization can be a freshly prepared basal culture medium, that is, the second cell differentiation culture medium used for carrying out the second time of differentiation of the trophoblast-like cells. Of course, the neutralization also can be carried out using serum. With the stem cell centrifugation, the stem cells can be effectively separated out intactly.

The embodiments of the present disclosure propose new solutions regarding the fact that the differentiation of the pluripotent stem cells into the mesenchymal stem cells at present is realized under 2D adherent conditions and various problems that would come up during its use, that is, the pluripotent stem cells are directly differentiated into the mesenchymal stem cells by utilizing their ability that they can be spheroidized and amplified under 3D suspension conditions, moreover, the differentiation has high efficiency, high yield, high purity, good performance, can meet the clinical requirements on a large amount of mesenchymal stem cells, and has a remarkable use value.

According to embodiments of the present disclosure, there is provided a method of differentiating pluripotent stem cells into mesenchymal stem cells having a biological activity under a 3D spheroidal suspension culture condition, comprising three steps:

Step 1: amplifying pluripotent stem cells in a 3D spheroidal suspension culture system, wherein the pluripotent stem cells naturally form spheroids under a non-adherent condition; sieving detached cell colonies with a cell strainer to form cell clusters of similar sizes; the cell clusters gradually form cell spheroids through a culturing; and during the culturing process, a tackifier is added to ensure that the stem cell spheroids do not fuse to form irregular shapes, thereby leading to a spontaneous differentiation and thus a quality degradation;

Step 2: replacing the amplification culture solution for pluripotent stem cells with a differentiation culture solution, wherein the differentiation culture solution is used in two stages, wherein for a first stage, the pluripotent stem cells are differentiated into trophoblast-like cells using BMP4 and A8301, the process of which takes 2-5 days; and then for a second stage, the culture solution is replaced with a differentiation culture solution, differentiating the trophoblast-like cells into the mesenchymal stem cells, the process of which takes about 20 days, each in form of cell spheroids; and Step 3, applying the mesenchymal stem cells, wherein the differentiated mesenchymal stem cell spheroids are packaged in a cell container such as a centrifuge tube, wherein up to 90% of the space within the container is filled with a stem cell culture medium, so that storage and transportation can be realized at room temperature, wherein if a culture flask is used, a flask cap can be directly tightened; the mesenchymal stem cell spheroids can maintain a motility rate of above 90% within 10 days and assure an excellent biological function; and after reaching a use site, mesenchymal stem cells can be directly used for tissue and organ regeneration and the like in form of spheroidal shape; and if intravascular injection is necessary, the mesenchymal stem cell spheroids are digested and dissociated into single cells for injection.

Preferably, in the first stage, components of the culture medium for differentiating to provide the mesenchymal stem cells include 1 uM A8301 and 10 ng/ml BMP4, and the basal culture medium is a DMEM low-sugar culture medium added with 20% serum substitute, 1% non-essential amino acid and 5% L-Glutamine.

Preferably, prior to a spheroidization of the stem cells, the pluripotent stem cell colonies conventionally cultured are detached and passed through the cell strainer with a same pore size to form cell clusters of a same size; and the cell clusters are subjected to a suspension culturing for 24-48 hours, preferably for 36 hours, to form cell spheroids.

Preferably, the same pore size is 50 microns.

Preferably, in the step of amplifying the pluripotent stem cells, a fluid substrate is an mTeSR1 cell culture medium, containing basic nutrients and an acid-base balance system as well as containing 10 uM Y27632.

Preferably, the tackifier is a food-grade additive which can improve the viscosity of the fluid substrate; preferably a methylcellulose, and a concentration is preferably of 0.2%-0.5%; wherein the food-grade tackifier does not result in a production of biotoxicity, is able to be metabolized, leaves no residue behind, has a high level of safety and is convenient to use.

Preferably, the stem cell spheroids, after collection, can be directly used or be used after being digested into single cells with trypsin, or the mesenchymal stem cells can be directly used in form of spheroids, for tissue and organ regeneration and the like, after that the stem cell spheroids have reached the use site.

Preferably, the non-biotoxic substrate is methylcellulose, and the methylcellulose is added to a fluid culture medium of active energy in a final concentration of 0.2%-0.3% to form a package substrate; and the non-biotoxic package substrate can also be a matrigel, a hydrogel, a food tackifier or a thickening agent.

Preferably, the pluripotent stem cells comprise induced pluripotent stem cells and embryonic stem cell lines, and comprise pluripotent stem cell lines from all vertebrates.

Preferably, the mesenchymal stem cell spheroids produced and prepared by means of the method provided here can directly satisfy the requirement of the differentiation for a bone, a cartilage and a fat, wherein the entire process is carried out with complete 3D culturing and without the process of 2D adherent.

Below the features and performances of the present disclosure are further described in detail in combination with examples.

Example 1

Firstly, Envy cells obtained from 2D adherent culturing were cultured to a degree of fusion of 80%, then washed with 1× PBS once, dissociated with 1× EDTA/PBS for 3 minutes and washed with 1× PBS once, then the Envy cells were collected by using mTeSR1, and 10 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 37° C., 5% carbon dioxide and 90% humidity, and in a culturing process, methylcellulose was added, with a concentration of 0.3% of a mass of an amplification culture medium. The mTeSR1 was replaced with a first cell differentiation culture medium on day 2, the culturing lasted 3 days, then the first cell differentiation culture medium was replaced with a second cell differentiation culture medium to continue the culturing 20 days. The first cell differentiation culture medium included BMP4, A8301 and a basal culture medium, and the basal culture medium included, in parts by weight, 74 parts of a DMEM low-sugar culture medium, 20 parts of serum substitute, 1 part of non-essential amino acid and 5 parts of L-Glutamine; the second cell differentiation culture medium was a basal culture medium. A concentration of BMP4 in the first cell differentiation culture medium was 10 ng/mL, and a concentration of A8301 in the first cell differentiation culture medium was 1 μM.

Then, the differentiated mesenchymal stem cell spheroids were packaged in a centrifuge tube, and up to 90% of a space within the centrifuge tube was filled with a stem cell culture medium.

Example 2

Firstly, Envy cells obtained from 2D adherent culturing were cultured to a degree of fusion of 78%, then washed with 1× PBS once, dissociated with 1× EDTA/PBS for 3 minutes and washed with 1× PBS once, then the Envy cells were collected by using mTeSR1, and 8 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 36° C., 4% carbon dioxide and 85% humidity, and in a culturing process, methylcellulose was added, with a concentration of 0.2% of a mass of an amplification culture medium. The mTeSR1 was replaced with a first cell differentiation culture medium on day 2, the culturing lasted 2 days, then the first cell differentiation culture medium was replaced with a second cell differentiation culture medium to continue the culturing 18 days. The first cell differentiation culture medium included BMP4, A8301 and a basal culture medium, and the basal culture medium included, in parts by weight, 72 parts of a DMEM low-sugar culture medium, 18 parts of serum substitute, 0.5 parts of non-essential amino acid and 3 parts of L-Glutamine; the second cell differentiation culture medium was a basal culture medium. A concentration of BMP4 in the first cell differentiation culture medium was 5 ng/mL, and a concentration of A8301 in the first cell differentiation culture medium was 0.6 μM.

Then, the differentiated mesenchymal stem cell spheroids were packaged in a centrifuge tube, and up to 90% of a space within the centrifuge tube was filled with a stem cell culture medium.

Example 3

Firstly, Envy cells obtained from 2D adherent culturing were cultured to a degree of fusion of 82%, then washed with 1× PBS once, dissociated with 1× EDTA/PBS for 3 minutes and washed with 1× PBS once, then the Envy cells were collected by using mTeSR1, and 12 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 39° C., 7% carbon dioxide and 92% humidity, and in a culturing process, methylcellulose was added, with a concentration of 0.5% of a mass of an amplification culture medium. The mTeSR1 was replaced with a first cell differentiation culture medium on day 2, the culturing lasted 5 days, then the first cell differentiation culture medium was replaced with a second cell differentiation culture medium to continue the culturing 22 days. The first cell differentiation culture medium included BMP4, A8301 and a basal culture medium, and the basal culture medium included, in parts by weight, 76 parts of a DMEM low-sugar culture medium, 22 parts of serum substitute, 1.5 parts of non-essential amino acid and 7 parts of L-Glutamine; the second cell differentiation culture medium was a basal culture medium. A concentration of BMP4 in the first cell differentiation culture medium was 15 ng/mL, and a concentration of A8301 in the first cell differentiation culture medium was 1.5 μM.

Then, the differentiated mesenchymal stem cell spheroids were packaged in a centrifuge tube, and up to 90% of a space within the centrifuge tube was filled with a stem cell culture medium.

Example 4

Firstly, Envy cells obtained from 2D adherent culturing were cultured to a degree of fusion of 81%, then washed with 1× PBS once, dissociated with 1× EDTA/PBS for 3 minutes and washed with 1× PBS once, then the Envy cells were collected by using mTeSR1, and 11 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 38° C., 6% carbon dioxide and 89% humidity, and in a culturing process, methylcellulose was added, with a concentration of 0.4% of a mass of an amplification culture medium. The mTeSR1 was replaced with a first cell differentiation culture medium on day 2, the culturing lasted 4 days, then the first cell differentiation culture medium was replaced with a second cell differentiation culture medium to continue the culturing 21 days. The first cell differentiation culture medium included BMP4, A8301 and a basal culture medium, and the basal culture medium included, in parts by weight, 75 parts of a DMEM low-sugar culture medium, 19 parts of serum substitute, 1.2 parts of non-essential amino acid and 6 parts of L-Glutamine; the second cell differentiation culture medium was a basal culture medium. A concentration of BMP4 in the first cell differentiation culture medium was 9 ng/mL, and a concentration of A8301 in the first cell differentiation culture medium was 0.6 μM.

Then, the differentiated mesenchymal stem cell spheroids were packaged in a culture flask, and up to 90% of a space within the culture flask was filled with a stem cell culture medium.

Example 5

Firstly, Envy cells obtained from 2D adherent culturing were cultured to a degree of fusion of 79%, then washed with 1× PBS once, dissociated with 1× EDTA/PBS for 3 minutes and washed with 1× PBS once, then the Envy cells were collected by using mTeSR1, and 9 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 37° C., 5% carbon dioxide and 90% humidity, and in a culturing process, methylcellulose was added, with a concentration of 0.3% of a mass of an amplification culture medium. The mTeSR1 was replaced with a first cell differentiation culture medium on day 2, the culturing lasted 3 days, then the first cell differentiation culture medium was replaced with a second cell differentiation culture medium to continue the culturing 20 days. The first cell differentiation culture medium included BMP4, A8301 and a basal culture medium, and the basal culture medium included, in parts by weight, 73 parts of a DMEM low-sugar culture medium, 21 parts of serum substitute, 0.9 parts of non-essential amino acid and 4 parts of L-Glutamine; the second cell differentiation culture medium was a basal culture medium. A concentration of BMP4 in the first cell differentiation culture medium was 12 ng/mL, and a concentration of A8301 in the first cell differentiation culture medium was 1.2 μM.

Then, the differentiated mesenchymal stem cell spheroids were packaged in a culture flask, and up to 90% of a space within the centrifuge tube was filled with a stem cell culture medium.

Example 6

Firstly, Envy cells obtained from 2D adherent culturing were cultured to a degree of fusion of 80%, then washed with 1× PBS once, dissociated with 1× EDTA/PBS for 3 minutes and washed with 1× PBS once, then the Envy cells were collected by using mTeSR1, and 10 μM of Y27632 was added.

Secondly, all suspension containing the Envy cells passed through a cell strainer with a pore size of 50 microns under pressure, and the cell suspension was placed in an ultra-low attachment culture dish for culturing, wherein culturing conditions were 38° C., 6% carbon dioxide and 90% humidity, and in a culturing process, methylcellulose was added, with a concentration of 0.4% of a mass of an amplification culture medium. The mTeSR1 was replaced with a first cell differentiation culture medium on day 2, the culturing lasted 4 days, then the first cell differentiation culture medium was replaced with a second cell differentiation culture medium to continue the culturing 19 days. The first cell differentiation culture medium included BMP4, A8301 and a basal culture medium, and the basal culture medium included, in parts by weight, 73 parts of a DMEM low-sugar culture medium, 20 parts of serum substitute, 1 part of non-essential amino acid and 5 parts of L-Glutamine; the second cell differentiation culture medium was a basal culture medium. A concentration of BMP4 in the first cell differentiation culture medium was 7 ng/mL, and a concentration of A8301 in the first cell differentiation culture medium was 1.1 μM.

Then, the differentiated mesenchymal stem cell spheroids were packaged in a culture flask, and up to 90% of a space within the culture flask was filled with a stem cell culture medium.

Comparative Example 1

Pluripotent stem cells were subjected to conventional 2D adherent culturing to be differentiated into mesenchymal stem cells.

Test Example

The mesenchymal stem cell spheroids prepared in Example 1 were perfused into a bone fibrous scaffold to carry out bone regeneration experiments (as shown in FIG. 2), specifically:

The collected mesenchymal stem cell spheroids were centrifuged at 100 rpm, then washed with 1× PBS twice, then the mesenchymal stem cell spheroids were re-suspended in a bone differentiation liquid, of which a concentration was adjusted to be 108 cells per milliliter, the bone fibrous scaffold that had been infiltrated in 1× PBS in advance for two days was taken out and 1× PBS was removed; then the bone fibrous scaffold was rinsed with the bone differentiation liquid; then the bone fibrous scaffold was repeatedly infiltrated with the suspension of mesenchymal stem cell spheroids, such that the mesenchymal stem cell spheroids slowly permeated and filled the bone fibrous scaffold, and stayed at a room temperature for 10 min, such that the mesenchymal stem cells adhered to the scaffold; a sufficient bone differentiation liquid was slowly added along an edge of the culture dish, till that the bone scaffold is completely soaked; upon staying at a room temperature for 30 min, the mesenchymal stem cells adhered to the scaffold; the culture dish was placed in a normal culture (37° C., 5% carbon dioxide and 90% humidity) environment for culturing, with the medium being replaced every 5 days; osteogenesis was achieved just after continuous culturing for 20 days.

The mesenchymal stem cell spheroids produced by the method of the present disclosure can sufficiently adhere to the human bone fibrous scaffold and grow. After a differentiation process for 20 days, the mesenchymal stem cells can be completely differentiated into bone tissues, two human bone fibrous scaffolds can be completely fused together and maintain certain mechanical strength. It has a huge value for bone regeneration and repair.

For the differentiation process of Example 1, upon analysis under a microscope, a process of FIG. 1 and results shown in the figure are obtained. FIG. 1A shows monolayer-cultured human pluripotent stem cells. FIGS. 1B, C and D show preparing stem cell spheroids through a slicing method by means of a cell strainer, morphologies thereof under a microscope, in which the cells are aggregated into spheroids of a uniform size and the diameter distribution of the cell spheroids thereof. FIG. 1E shows cell morphologies of the mesenchymal stem cells cultured and differentiated in the differentiation culture solution under a microscope, wherein the cells still maintain morphologies under 3D conditions, that is, aggregating into spheroids of a uniform size. FIG. 1F shows cell morphologies of the mesenchymal stem cells under a microscope after being digested and dissociated and returning to grow under 2D conditions, wherein the cells are fusiform with different lengths. It can be seen from FIG. 1 that the mesenchymal stem cells can maintain a high survival rate at a room temperature (AC) after aggregation into spheroids.

It can be seen from FIG. 2C of FIG. 2 that the two fibrous scaffolds in FIG. 2A, after being fused by the mesenchymal stem cells, can be held by tweezers without fracture and have certain physical strength.

It can be seen from FIG. 3 that a great amount of the mesenchymal stem cell spheroids can be produced in a 200 ml system through 3D spheroidal differentiation, while a method of 2D adherent differentiating method requires a doubled cell culture dish as shown in the figure.

Figure 4:
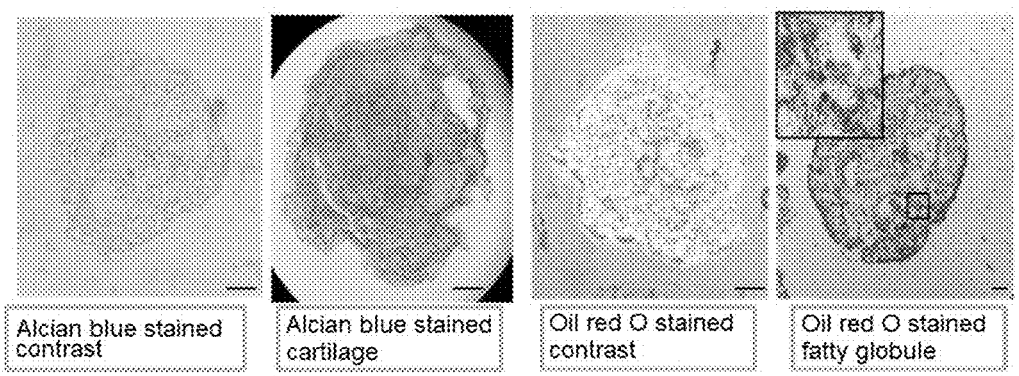
FIG. 4 shows that the mesenchymal stem cell spheroids obtained in Example 1 can be directly differentiated in vitro into cartilage spheroids and fat globules, and stained with a cartilage specific dye Alcian blue and with a fatty oil drop specific dye oil red O.

It can be seen from FIG. 4 that the mesenchymal stem cell spheroids obtained from the 3D spheroidal differentiation can be directly differentiated in vitro into cartilage spheroids and fat globules, and can be stained with a cartilage specific dye Alcian blue and with a fatty oil drop specific dye oil red O.

By comparing yields and consumptions of differentiation of the pluripotent stem cells into the mesenchymal stem cells in Example 1 and of the conventional 2D adherent differentiation method in the comparative example, results are shown in Table 1.

regeneration and beauty industry. Furthermore, the mesenchymal stem cells produced by means of the method of the present disclosure have no pluripotent stem cell residue, have a high level of safety, and would not result in tumors such as teratoma after being injected into a mouse body having immune deficiency.

Compared with the mesenchymal stem cells obtained in the 2D differentiation manner, the method of the present disclosure is less time-consuming and highly efficient, and has high differentiation purity, moreover, the mesenchymal stem cells have more excellent proliferation in vitro ability, are not prone to senescence, and have stronger anti-apoptotic ability. Moreover, with the spheroidal property of the mesenchymal stem cells, it can be assured that the mesenchymal stem cells can survive for one week at a room temperature, while the biological activity thereof will not be affected. The survival rate at a room temperature after 7-10 days is up to 90%, and after restoration to the conventional culture conditions, they still have a growth rate similar to that of normal control cells, a lower senescence degree and similar biological functions including the ability of directional differentiation into various tissues (bone, cartilage and fat) and immunomodulation functions.

Besides, the differentiation method of the embodiments of the present disclosure is simple and reliable, low in price, stable and efficient, there is no need to maintain the temperature or a specific gas concentration in the whole process, and the method can be directly used to the treatment of various inflammations or traumas immediately and in situ. In two types of experimental models of mice enterocolitis caused by chemical substances, the intraperitoneal injection of the mesenchymal stem cells preserved at a room temperature for 7 days can still effectively protect the mice from intestinal injury and weight loss. It is confirmed from pathological section that the injected mesenchymal stem cells can migrate to injured intestinal tissues to inhibit inflammatory response and promote tissue regeneration of an injured intestinal wall. Thus, the present disclosure will have extremely high level of scientific and socioeconomic benefits when being popularized.

The above-mentioned are for some but not all of examples of the present disclosure. The detailed description of the examples of the present disclosure is not intended to limit the scope of protection of the present disclosure, but merely represents chosen examples of the present disclosure. All the other examples obtained by a person ordinarily skilled in the

TABLE 1

|  | cell number ($10^7$) | cell density/ml | days | passaging time | culture medium (ml) | culture vessel | total culture medium (ml) | buffer quantity (ml) | trypsin (ml) |
|---|---|---|---|---|---|---|---|---|---|
| Example 1 | 7 | $7.0 \times 10^5$ | 20 | 0 | 100 | 100 ml bag × 1 | 300 | 0 | 0 |
| Comparative Example | 4.2 | $2.5 \times 10^5$ | 39 | 5 | 165 | T75 flask × 21 | 555 | 420 | 63 |

It can be seen from Table 1 that compared with normal 2D adherent differentiation culturing, the 3D suspension culturing method of Example 1 renders bigger cell density, and uses less vessels, culture medium, buffer and so on.

To sum up, in the method provided in the embodiments of the present disclosure, $10^8$ mesenchymal stem cells can be obtained from the pluripotent stem cells within 25 days by means of a 200 ml culture bag, and these mesenchymal stem cells can be directly differentiated into fat, bone and cartilage, which has a huge value for uses in tissue and organ art without paying inventive efforts, based on the examples of the present disclosure, shall fall within the scope of protection of the present disclosure.

The invention claimed is:

1. A method of differentiating pluripotent stem cells into mesenchymal stem cells, wherein the method comprises: differentiating, completely under 3D suspension conditions, pluripotent stem cells into trophoblast-like cells using bone morphogenetic protein-4 (BMP4) and A8301, then differentiating the trophoblast-like cells into mesenchymal stem cells, wherein neither of the two differentiation processes needs passaging or replacement of a culture container, wherein the pluripotent stem cells are placed in a first cell differentiation culture medium containing the BMP4 and the A8301 to carry out first differentiation culturing, then second differentiation culturing is carried out in a second cell differentiation culture medium for the trophoblast-like cells obtained in the first differentiation culturing, to obtain the mesenchymal stem cells, wherein the first differentiation culturing lasts for 2-5 days, and the second differentiation culturing lasts for 18-22 days, wherein the first cell differentiation culture medium comprises the BMP4, the A8301 and a basal culture medium, and the basal culture medium comprises, in parts by weight, 72-76 parts of a Dulbecco's modified eagle medium (DMEM) low-sugar culture medium, 18-22 parts of serum substitute, 0.5-1.5 parts of non-essential amino acid and 3-7 parts of L-Glutamine; and the second cell differentiation culture medium is the basal culture medium.

2. The method according to claim 1, wherein a concentration of the BMP4 in the first cell differentiation culture medium is 5-15 ng/mL, and a concentration of the A8301 in the first cell differentiation culture medium is 0.5-1.5 μM.

3. The method according to claim 1, wherein the pluripotent stem cells are obtained through amplification culturing of initial pluripotent stem cells, and the amplification culturing of the initial pluripotent stem cells comprises cutting cell colonies of the initial pluripotent stem cells with a cell strainer into cell clusters, and then performing suspension culturing on the cell clusters in an amplification culture medium.

4. The method according to claim 3, wherein in the suspension culturing of the cell clusters, a tackifier, a extracellular matrix, a hydrogel or a thickening agent is added.

5. The method according to claim 4, wherein the tackifier is a food-grade additive.

6. The method according to claim 5, wherein the tackifier is methylcellulose, and a concentration of added methylcellulose is 0.2%-0.5% of a mass of the amplification culture medium.

7. The method according to claim 3, wherein the amplification culture medium is a pluripotent stem cell culture medium, and the pluripotent stem cell culture medium is added with Y27632, and a concentration of the Y27632 in the mTeSR1 cell culture medium is 8-12 μM.

8. The method according to claim 3, wherein a pore size of the cell strainer is 50 microns.

9. The method according to claim 3, wherein the cell colonies of the initial pluripotent stem cells are collected after initial pluripotent stem cells are adherently cultured to a degree of fusion of 78-82% and then washed with 1×PBS.

* * * * *